United States Patent
Syed Shah et al.

(10) Patent No.: US 12,201,837 B2
(45) Date of Patent: Jan. 21, 2025

(54) APPARATUSES AND METHODS FOR SETTING AN ELECTRICAL DOSE

(71) Applicant: Neuros Medical, Inc., Aliso Viejo, CA (US)

(72) Inventors: Nemath Syed Shah, Lyndhurst, OH (US); Zi-Ping Fang, Beachwood, OH (US)

(73) Assignee: Neuros Medical, Inc., Aliso Viejo, CA (US)

( * ) Notice: Subject to any disclaimer, the term of this patent is extended or adjusted under 35 U.S.C. 154(b) by 0 days.

(21) Appl. No.: 18/346,499

(22) Filed: Jul. 3, 2023

(65) Prior Publication Data

US 2024/0001122 A1    Jan. 4, 2024

Related U.S. Application Data (63) Continuation of application No. 17/455,392, filed on Nov. 17, 2021, now Pat. No. 11,730,963, which is a
(Continued)

(51) Int. Cl.
*A61N 1/36* (2006.01)
*A61N 1/05* (2006.01)

(52) U.S. Cl.
CPC ....... *A61N 1/36071* (2013.01); *A61N 1/0556* (2013.01); *A61N 1/36153* (2013.01); *A61N 1/36171* (2013.01)

(58) Field of Classification Search
CPC .............. A61N 1/36071; A61N 1/0556; A61N 1/36153; A61N 1/36171; A61N 1/361;
(Continued)

(56) References Cited

U.S. PATENT DOCUMENTS 3,738,368 A    6/1973 Avery et al.
4,155,366 A    5/1979 Di Mucci
(Continued)

FOREIGN PATENT DOCUMENTS

CN    102573986 A    7/2012
DE    202010015346 U1    4/2011
(Continued)

OTHER PUBLICATIONS

Ackermann et al.; Effect of bipolar cuff electrode design on block thresholds in high-frequency electrical neural conduction block; IEEE Transactions on Neural Systems and Rehabilitation Engineering; 17(5); pp. 469-477; Oct. 1, 2009.
(Continued)

*Primary Examiner* — Yingchuan Zhang
*Assistant Examiner* — Anh-Khoa N Dinh
(74) *Attorney, Agent, or Firm* — Shay Glenn LLP (57) ABSTRACT

Methods and apparatuses for setting a therapeutic dose of a neuromodulator implanted into a patient. The therapeutic dose typically includes a therapeutic dose duration including a ramp-up time to reach a peak modulation voltage and a sustained peak modulation time during which the voltage is sustained at the peak modulation voltage. The methods and apparatuses may use a testing ramp to identify a peak modulation voltage that is patient-specific and provides a maximized therapeutic effect while remaining comfortably tolerable by the patient during the application of energy by the neuromodulator.

18 Claims, 8 Drawing Sheets

Related U.S. Application Data continuation of application No. 16/379,053, filed on Apr. 9, 2019, now Pat. No. 11,213,682.

(60) Provisional application No. 62/655,122, filed on Apr. 9, 2018.

(58) Field of Classification Search
CPC .............. A61N 1/36132; A61N 1/3615; A61N 1/37247; A61N 1/0551; A61N 1/36139; A61N 1/3702; A61N 1/39622; A61N 1/36021; A61N 1/36114; A61N 1/39624; A61N 2/006; A61N 1/37211; A61N 1/025; A61N 1/0534; A61N 1/3614; A61N 1/36185; A61N 1/3718; A61N 1/37282; A61N 1/36067; A61N 1/36175; A61N 1/36064; A61N 1/36082; A61N 1/36125; A61N 1/36128; A61N 1/36146; A61N 1/3621
See application file for complete search history.

(56) References Cited

U.S. PATENT DOCUMENTS

| | | | |
|---|---|---|---|
| 4,573,481 A | 3/1986 | Bullara | |
| 4,602,624 A | 7/1986 | Naples et al. | |
| 4,979,511 A | 12/1990 | Terry | |
| 5,143,067 A | 9/1992 | Rise et al. | |
| 5,324,322 A | 6/1994 | Grill et al. | |
| 5,653,739 A | 8/1997 | Maurer et al. | |
| 5,755,750 A | 5/1998 | Petruska et al. | |
| 5,964,702 A | 10/1999 | Grill, Jr. et al. | |
| 6,058,331 A | 5/2000 | King | |
| 6,275,735 B1 | 8/2001 | Jarding et al. | |
| 6,292,703 B1 | 9/2001 | Meier et al. | |
| 6,456,866 B1 | 9/2002 | Tyler et al. | |
| 6,699,275 B1 | 3/2004 | Knudson et al. | |
| 6,735,475 B1 | 5/2004 | Whitehurst et al. | |
| 6,760,626 B1 | 7/2004 | Boveja | |
| 6,836,685 B1 | 12/2004 | Fitz | |
| 6,860,851 B2 | 3/2005 | Knudson et al. | |
| 6,871,099 B1 | 3/2005 | Whitehurst et al. | |
| 7,076,307 B2 | 7/2006 | Boveja et al. | |
| 7,167,750 B2 | 1/2007 | Knudson et al. | |
| 7,201,757 B2 | 4/2007 | Knudson et al. | |
| 7,292,890 B2 | 11/2007 | Whitehurst et al. | |
| 7,295,876 B1 | 11/2007 | Erickson | |
| 7,302,296 B1 | 11/2007 | Hoffer | |
| 7,324,852 B2 | 1/2008 | Barolat et al. | |
| 7,389,145 B2 | 6/2008 | Kilgore et al. | |
| 7,444,183 B2 | 10/2008 | Knudson et al. | |
| 7,463,927 B1 | 12/2008 | Chaouat | |
| 7,489,966 B2 | 2/2009 | Leinders et al. | |
| 7,555,345 B2 | 6/2009 | Wahlstrand et al. | |
| 7,616,990 B2 | 11/2009 | Chavan et al. | |
| 7,761,166 B2 | 7/2010 | Giftakis et al. | |
| 7,839,415 B2 | 11/2010 | Hillard et al. | |
| 7,860,570 B2 | 12/2010 | Whitehurst et al. | |
| 7,894,905 B2 | 2/2011 | Pless et al. | |
| 7,894,906 B2 | 2/2011 | Shuros | |
| 7,979,131 B2 | 7/2011 | Feler et al. | |
| 8,027,718 B2 | 9/2011 | Spinner et al. | |
| 8,060,208 B2 | 11/2011 | Kilgore et al. | |
| 8,060,209 B2 | 11/2011 | Jaax et al. | |
| 8,108,052 B2 | 1/2012 | Boling | |
| 8,116,882 B2 | 2/2012 | Kowalczewski | |
| 8,170,675 B2 | 5/2012 | Alataris et al. | |
| 8,185,207 B2 | 5/2012 | Molnar et al. | |
| 8,219,202 B2 | 7/2012 | Giftakis et al. | |
| 8,224,453 B2 | 7/2012 | De Ridder | |
| 8,380,318 B2 | 2/2013 | Kishawi et al. | |
| 8,452,417 B2 | 5/2013 | Navarro | |
| 8,467,879 B1 | 6/2013 | Whitehurst et al. | |
| 8,498,711 B2 | 7/2013 | Roche | |
| 8,504,147 B2 | 8/2013 | Deem et al. | |
| 8,521,291 B1 | 8/2013 | Cholette et al. | |
| 8,560,075 B2 | 10/2013 | Covalin | |
| 8,594,796 B2 | 11/2013 | Roche | |
| 8,600,505 B2 | 12/2013 | Libbus et al. | |
| 8,676,329 B2 | 3/2014 | Wacnik et al. | |
| 8,676,331 B2 | 3/2014 | Parker | |
| 8,712,547 B2 | 4/2014 | Whitehurst et al. | |
| 8,731,676 B2 | 5/2014 | Fang et al. | |
| 8,738,140 B2 | 5/2014 | De Ridder | |
| 8,755,893 B2 | 6/2014 | Gross et al. | |
| 8,761,892 B2 | 6/2014 | Weisgarber et al. | |
| 8,788,045 B2 | 7/2014 | Gross et al. | |
| 8,805,518 B2 | 8/2014 | King et al. | |
| 8,903,502 B2 | 12/2014 | Perryman et al. | |
| 8,923,975 B2 | 12/2014 | Bradley | |
| 8,965,516 B2 | 2/2015 | Bennett et al. | |
| 8,977,362 B2 | 3/2015 | Saab | |
| 8,983,612 B2 | 3/2015 | Fang et al. | |
| 8,983,614 B2 | 3/2015 | Kilgore et al. | |
| 9,031,658 B2 | 5/2015 | Chiao et al. | |
| 9,037,248 B2 | 5/2015 | Durand et al. | |
| 9,089,700 B2 | 7/2015 | Hlavka et al. | |
| 9,095,699 B2 | 8/2015 | Rosenberg et al. | |
| 9,132,272 B2 | 9/2015 | Alves et al. | |
| 9,259,575 B2 | 2/2016 | Zhao et al. | |
| 9,295,840 B1 | 3/2016 | Thacker et al. | |
| 9,295,841 B2 | 3/2016 | Fang et al. | |
| 9,327,121 B2 | 5/2016 | Thacker et al. | |
| 9,339,655 B2 | 5/2016 | Carbunaru | |
| 9,387,325 B1 | 7/2016 | Min et al. | |
| 9,403,008 B2 | 8/2016 | Howard | |
| 9,403,014 B2 | 8/2016 | Kilgore et al. | |
| 9,409,019 B2 | 8/2016 | Walker et al. | |
| 9,421,372 B2 | 8/2016 | Mashiach et al. | |
| 9,604,062 B2 | 3/2017 | Carroll | |
| 9,630,011 B2 | 4/2017 | Lipani | |
| 9,694,181 B2 | 7/2017 | Bhadra et al. | |
| 9,814,881 B2 | 11/2017 | Moffitt | |
| 9,884,189 B2 | 2/2018 | Boggs | |
| 9,884,192 B2 | 2/2018 | Kilgore et al. | |
| 9,889,293 B2 | 2/2018 | Siegel et al. | |
| 9,931,510 B2 | 4/2018 | Hou et al. | |
| 9,937,348 B1 | 4/2018 | Bradley | |
| 9,956,398 B2 | 5/2018 | Callegari et al. | |
| 10,086,201 B2 | 10/2018 | Chang et al. | |
| 10,105,541 B2 | 10/2018 | Kishawi et al. | |
| 10,149,978 B1 | 12/2018 | Park | |
| 10,159,838 B2 | 12/2018 | Kim et al. | |
| 10,195,434 B2 | 2/2019 | Bhadra et al. | |
| 10,238,872 B2 | 3/2019 | Pivonka et al. | |
| 10,258,805 B2 | 4/2019 | Reed et al. | |
| 10,286,213 B2 | 5/2019 | Fletcher et al. | |
| 10,300,273 B2 | 5/2019 | Rooney et al. | |
| 10,315,034 B2 | 6/2019 | Hou et al. | |
| 10,328,256 B1 | 6/2019 | Gliner | |
| 10,390,877 B2 | 8/2019 | Heggeness et al. | |
| 10,456,575 B2 | 10/2019 | Kilgore et al. | |
| 10,617,870 B2 | 4/2020 | Kilgore et al. | |
| 10,632,309 B2 | 4/2020 | McGee et al. | |
| 10,675,469 B2 | 6/2020 | Annoni et al. | |
| 10,722,703 B2 | 7/2020 | Mitchell | |
| 10,758,723 B2 | 9/2020 | Fang et al. | |
| 10,780,270 B2 | 9/2020 | Schepis et al. | |
| 10,786,669 B2 | 9/2020 | Rajguru et al. | |
| 10,799,701 B2 | 10/2020 | Lee | |
| 10,828,491 B2 | 11/2020 | Schepis et al. | |
| 10,864,373 B2 | 12/2020 | Bhadra et al. | |
| 10,894,159 B2 | 1/2021 | De Ridder | |
| 10,926,092 B2 | 2/2021 | Esteller et al. | |
| 10,953,228 B2 | 3/2021 | Perryman et al. | |
| 10,967,183 B2 | 4/2021 | Yakovlev et al. | |
| 11,007,364 B2 | 5/2021 | Carroll | |
| 11,027,126 B2 | 6/2021 | Ackermann et al. | |
| 11,071,863 B2 | 7/2021 | Torgerson | |
| 11,116,965 B2 | 9/2021 | Snyder | |
| 11,116,975 B2 | 9/2021 | Oron et al. | |
| 11,167,129 B2 | 11/2021 | Parker | |
| 11,213,682 B2 | 1/2022 | Syed Shah et al. | |
| 11,235,146 B2 | 2/2022 | Boggs et al. | |

(56) References Cited

U.S. PATENT DOCUMENTS

| | | |
|---|---|---|
| 11,247,053 B2 | 2/2022 | Rajguru et al. |
| 11,253,705 B1 | 2/2022 | John |
| 11,278,718 B2 | 3/2022 | Faltys et al. |
| 11,311,726 B2 | 4/2022 | Vansickle et al. |
| 11,331,489 B2 | 5/2022 | Johanek |
| 11,331,493 B2 | 5/2022 | Pivonka et al. |
| 11,344,726 B2 | 5/2022 | Bennett et al. |
| 11,344,729 B1 | 5/2022 | Single et al. |
| 11,413,458 B2 | 8/2022 | Fang et al. |
| 11,730,963 B2 | 8/2023 | Syed Shah et al. |
| 11,752,331 B2 | 9/2023 | Snyder |
| 2002/0055779 A1 | 5/2002 | Andrews |
| 2002/0198572 A1 | 12/2002 | Weiner |
| 2003/0144709 A1 | 7/2003 | Zabara et al. |
| 2004/0015205 A1 | 1/2004 | Whitehurst et al. |
| 2004/0111139 A1 | 6/2004 | McCreery |
| 2004/0147977 A1 | 7/2004 | Petrofsky |
| 2004/0243182 A1 | 12/2004 | Cohen et al. |
| 2005/0131485 A1 | 6/2005 | Knudson et al. |
| 2005/0137648 A1 | 6/2005 | Cosendai et al. |
| 2005/0143789 A1 | 6/2005 | Whitehurst et al. |
| 2005/0149148 A1 | 7/2005 | King |
| 2005/0149154 A1 | 7/2005 | Cohen et al. |
| 2006/0025832 A1 | 2/2006 | O'Keeffe et al. |
| 2006/0030919 A1 | 2/2006 | Mrva et al. |
| 2006/0184211 A1 | 8/2006 | Gaunt et al. |
| 2006/0195158 A1 | 8/2006 | Cory |
| 2006/0270944 A1 | 11/2006 | King et al. |
| 2006/0271137 A1 | 11/2006 | Stanton-Hicks |
| 2006/0293721 A1 | 12/2006 | Tarver et al. |
| 2007/0043400 A1 | 2/2007 | Donders |
| 2007/0142863 A1 | 6/2007 | Bradley |
| 2007/0185549 A1 | 8/2007 | Zdeblick |
| 2008/0027505 A1 | 1/2008 | Levin et al. |
| 2008/0046055 A1 | 2/2008 | Durand et al. |
| 2008/0086180 A1 | 4/2008 | Ben-Ezra et al. |
| 2008/0172116 A1 | 7/2008 | Mrva et al. |
| 2008/0183226 A1 | 7/2008 | Buras et al. |
| 2008/0228194 A1 | 9/2008 | Westlund et al. |
| 2008/0319511 A1 | 12/2008 | Pless |
| 2009/0069738 A1 | 3/2009 | Rossing et al. |
| 2009/0083070 A1 | 3/2009 | Giftakis et al. |
| 2009/0204173 A1 | 8/2009 | Fang et al. |
| 2009/0281595 A1 | 11/2009 | King et al. |
| 2010/0121408 A1 | 5/2010 | Imran et al. |
| 2010/0152808 A1 | 6/2010 | Boggs, II |
| 2010/0168820 A1 | 7/2010 | Maniak et al. |
| 2010/0211135 A1 | 8/2010 | Caparso et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0071593 A1 | 3/2011 | Parker et al. |
| 2011/0230701 A1 | 9/2011 | Simon et al. |
| 2011/0313488 A1 | 12/2011 | Hincapie Ordonez et al. |
| 2012/0016439 A1 | 1/2012 | Alataris et al. |
| 2012/0083709 A1 | 4/2012 | Parker et al. |
| 2012/0083856 A1 | 4/2012 | Thacker et al. |
| 2012/0089199 A1 | 4/2012 | Bolea et al. |
| 2012/0232615 A1 | 9/2012 | Barolat et al. |
| 2012/0253261 A1 | 10/2012 | Poletto et al. |
| 2013/0035735 A1 | 2/2013 | Kroll |
| 2013/0289664 A1 | 10/2013 | Johanek |
| 2013/0289667 A1* | 10/2013 | Wacnik ............. A61N 1/36171 607/2 |
| 2014/0046398 A1 | 2/2014 | Sachs et al. |
| 2014/0188186 A1 | 7/2014 | Barolat et al. |
| 2014/0228905 A1 | 8/2014 | Bolea |
| 2015/0230809 A1 | 8/2015 | Becker |
| 2016/0256685 A1 | 9/2016 | Haessler |
| 2016/0361542 A1 | 12/2016 | Kaula et al. |
| 2017/0007836 A1 | 1/2017 | Nassif |
| 2017/0095667 A1 | 4/2017 | Yakovlev et al. |
| 2017/0239486 A1 | 8/2017 | Suryavanshi |
| 2017/0319381 A1 | 11/2017 | Rogers |
| 2017/0333701 A1 | 11/2017 | Bradley et al. |
| 2017/0348532 A1 | 12/2017 | Moffitt et al. |
| 2018/0008827 A1 | 1/2018 | Dolev et al. |
| 2018/0021577 A1 | 1/2018 | Phillips |
| 2018/0043172 A1 | 2/2018 | Serrano Carmona |
| 2018/0056066 A1 | 3/2018 | Boggs et al. |
| 2018/0140835 A1 | 5/2018 | Sharma |
| 2018/0333576 A1 | 11/2018 | Rigaux |
| 2019/0151659 A1 | 5/2019 | Mishra et al. |
| 2019/0184170 A1 | 6/2019 | Knudson et al. |
| 2019/0275328 A1 | 9/2019 | Zitnik et al. |
| 2019/0358455 A1 | 11/2019 | Lin et al. |
| 2019/0358466 A1 | 11/2019 | Leung et al. |
| 2019/0374779 A1 | 12/2019 | Kilgore et al. |
| 2021/0069501 A1 | 3/2021 | Molnar et al. |
| 2021/0069504 A1 | 3/2021 | Hunsberger et al. |
| 2021/0113840 A1 | 4/2021 | Bhadra et al. |
| 2021/0154478 A1 | 5/2021 | Hincapie Ordonez et al. |
| 2021/0220642 A1 | 7/2021 | Fang et al. |
| 2021/0236820 A1 | 8/2021 | Parker et al. |
| 2021/0244952 A1 | 8/2021 | Iorio et al. |
| 2021/0252288 A1 | 8/2021 | Lin et al. |
| 2021/0260381 A1 | 8/2021 | Kilgore et al. |
| 2021/0283398 A1 | 9/2021 | Kibler et al. |
| 2021/0283401 A1 | 9/2021 | Tai |
| 2021/0308456 A1 | 10/2021 | Gliner et al. |
| 2022/0008723 A1 | 1/2022 | Hsu et al. |
| 2022/0016421 A1 | 1/2022 | Boggs et al. |
| 2022/0023634 A1 | 1/2022 | Parker et al. |
| 2022/0023635 A1 | 1/2022 | Pepin et al. |
| 2022/0023648 A1 | 1/2022 | Doan et al. |
| 2022/0032060 A1 | 2/2022 | Bhadra et al. |
| 2022/0152393 A1 | 5/2022 | Kent et al. |
| 2022/0176108 A1 | 6/2022 | Linden et al. |
| 2022/0339446 A1 | 10/2022 | Fang et al. |

FOREIGN PATENT DOCUMENTS

| | | |
|---|---|---|
| EP | 3219357 A1 | 9/2017 |
| JP | 2009522015 A | 6/2009 |
| JP | 2012130579 A | 7/2012 |
| WO | WO00/61222 A1 | 10/2000 |
| WO | WO2005/105202 A1 | 11/2005 |
| WO | WO2007/117347 A1 | 10/2007 |
| WO | WO2009/079270 A1 | 6/2009 |
| WO | WO2012/159002 A8 | 11/2012 |
| WO | WO2018/033855 A1 | 2/2018 |
| WO | WO2018/067239 A1 | 4/2018 |
| WO | WO2018/106839 A2 | 6/2018 |
| WO | WO2020/041323 A1 | 2/2020 |

OTHER PUBLICATIONS

Ackermann et al.; Electrical conduction block in large nerves: high frequency current delivery in the nonhuman primate; Muscle and Nerve. 43(6); pp. 897-899; Jun. 2011.

Becker et al.; Essentials of local anesthetic pharmacology; Anesthesia progress; 53(3); pp. 98-109; Sep. 2006.

Bhadra et al.; High-frequency electrical conduction block of mammalian peripheral motor nerve; Muscle and Nerve; 32(6); pp. 782-790; Dec. 2005.

Bhadra et al.; Simulation of high-frequency sinusoidal electrical block of mammalian myelinated axons; Journal of Computational Neuroscience; 22(3); pp. 313-326; Jun. 1, 2007.

Bouaziz et al., Neurologic complication of peripheral neural blockade. In Cousins and Bridenbaugh's Neural blockade in clinical anesthesia and pain medicine, 4th ed. (Cousins et al., eds.); Ch. 20; Lippincott Williams and Wilkins; pp. 464-477; (the year of publication is sufficiently earlier than the effective U.S. filing date and any foreign priority date so that the particular month of publication is not in issue) 2009.

Cleeland et al.; Pain assessment: global use of the Brief Pain Inventory; Annals, Academy of Medicine, Singapore; 23(2); pp. 129-138; Mar. 1994.

(56) References Cited

OTHER PUBLICATIONS

Dickinson et al.; Maldynia: pathophysiology and management of neuropathic and maladaptive pain à report of the AMA Council on Science and Public Health; Pain Medicine; 11(11); pp. 1635-1653; Nov. 1, 2010.

Dworkin et al.; Interpreting the clinical importance of treatment outcomes in chronic pain clinical trials: IMMPACT recommendations; The Journal of Pain; 9(2); pp. 105-121; Feb. 1, 2008.

Fisher et al.; Chronic stability and selectivity of four-contact spiral nerve-cuff electrodes in stimulating the human femoral nerve; J. Neural Eng.; 6(4); pp. 1-16; Aug. 2009.

Flor et al.; Phantom limb pain: a case of maladaptive CNS plasticity? Nature Reviews Neuroscience; 7(11); pp. 873-881; Nov. 2006.

Fyfe, N.; An audit of amputation levels in patients referred for prosthetic rehabilitation; Prosthetics and Orthotics International; 14(2); pp. 67-70; Aug. 1990.

Gerges et al.; Frequency-and amplitude-transitioned waveforms mitigate the onset response in high-frequency nerve block; Journal of Neural Engineering; 7(6); pp. 1-17; Dec. 2010.

Guse et al.; Outcomes of the surgical treatment of peripheral neuromas of the hand and forearm: a 25-year comparative outcome study; Annals of plastic surgery; 71(6); pp. 654-658; (abstract) Dec. 1, 2013.

Hadzic et al.; Neurologic complications of peripheral nerve blocks. In Peripheral nerve blocks: principles and practice, 3rd ed. (Hadzic and Vloka, eds.); Ch. 6; New York: McGraw-Hill; pp. 67-77; Sep. 20, 2004.

Haroutounian et al.; Primary afferent input critical for maintaining spontaneous pain in peripheral neuropathy; PAIN; 155(7); pp. 1272-1279 (abstract); Jul. 1, 2014.

Hsu et al.; Postamputation pain: epidemiology, mechanisms, and treatment; Journal of Pain Research; 6; pp. 121-136; Feb. 12, 2013.

Keller et al.; Validity of the brief pain inventory for use in documenting the outcomes of patients with noncancer pain; The Clinical Journal of Pain; 20(5); pp. 309-318; Sep. 1, 2004.

Kilgore et al.; Block of mammalian motor nerve conduction using high frequency alternating current; 10th Annual Conference of International FES Society; Montreal, Canada; pp. 479-481; Jul. 2005.

Kilgore et al.; Nerve conduction block utilizing high-frequency alternating current; Med. Biol. Eng. Comput.; 42(3); pp. 394-406; May 1, 2004.

Kilgore et al.; Reversible nerve conduction block using kilohertz frequency alternating current; Neuromodulation: Technology at the Neural Interface; 17(3); pp. 242-255; Apr. 2014.

Kumar et al.; Spinal cord stimulation versus conventional medical management for neuropathic pain: a multicentre randomised controlled trial in patients with failed back surgery syndrome; Pain; 132(1-2); pp. 179-188; Nov. 1, 2007.

Leland et al.; American war and military operations casualties: lists and statistics. Congressional Research Service; CRS Report to Congress; RL32492; pp. 1-30; Feb. 26, 2010.

Lewin-Kowalik et al.; Prevention and management of painful neuroma; Neurol Med Chir (Tokyo); 46(2); pp. 62-68; Feb. 2006.

Melzack et al.; Pain mechanisms: a new theory; Science; 150(3699); pp. 971-979; Nov. 19, 1965.

Miles et al.; Effects of ramped amplitude waveforms on the response of high-frequency mammalian nerve block; Journal of Neural Engineering; 4(4); pp. 390-398; Nov. 12, 2007.

Naples et al.; A spiral nerve cuff electrode for peripheral nerve stimulation; IEEE Transactions on Biomedical Engineering; 35(11); pp. 905-916; Nov. 1988.

Narang et al.; Functional capabilities of lower limb amputees; Prosthetics and Orthotics International; 8(1); pp. 43-51; Jan. 1, 1984.

NLLIC Staff. Fact Sheet. Amputation Statistics by Cause Limb Loss in the United States. Amputee Coalition of America (2008) 2 pages; retrieved from internet site http://www.amputee-coalitionsorg/fact_sheets/amp_stats_cause.pdf; Accessed Aug. 26, 2014; (the year of publication is sufficiently earlier than the effective U.S. filing date and any foreign priority date so that the particular month of publication is not in issue) 2008.

North et al.; Spinal cord stimulation versus re-operation in patients with failed back surgery syndrome: an international multicenter randomized controlled trial (Evidence study); Neuromodulation: Technology at the Neural Interface; 14(4); pp. 330-336; Jul. 2011.

Page et al.; Oral Posters—Intrathecal Drug Delivery for Pain and Spasticity: 2013 1630-1640; Spine; 11 Jun.-004. Effect of intrathecal intermittent boluses and morphine concerntration on the incidence of inflammatory mass in a canine model; International Modulation Society; pp. 272-273; Jun. 11, 2013.

Pohjolainen et al.; Prosthetic use and functional and social outcome following major lower limb amputation; Prosthetics and Orthotics Intl.; 14(2); pp. 75-79; Jan. 1, 1990.

Polasek et al.; Stimulation stability and selectivity of chronically implanted multicontact nerve cuff electrodes in the human upper extremity; IEEE Transactions on Neural Systems and Rehabilitation Engineering: 17(5); pp. 428-437; Oct. 2009.

Saper et al.; Occipital nerve stimulation for the treatment of intractable chronic migraine headache: ONSTIM feasibility study; Cephalalgia; 31(3); pp. 271-285; Feb. 2011.

Schoppen et al.; Physical, mental, and social predictors of functional outcome in unilateral lower-limb amputees; Arch Phys Med Rehabil; 84(6); pp. 803-811; Jun. 1, 2003.

Sikka; Facial expression analysis for estimating pain in clinical settings; In Proceedings of the 16th International Conference on Multimodal Interaction; pp. 349-353; Nov. 2014.

Soin et al.; High-frequency electrical nerve block for post amputation pain: a pilot study; Neuromodulation; 16(5); 9 pages; Sep. 1, 2013.

Soin et al.; Feasibility study on high-frequency electrical nerve block for amputation pain; Neuromodulation; 14(6); p. 561; Nov. 1, 2011.

Subedi et al.; Phantom limb pain: mechanisms and treatment approaches; Pain Research and Treatment; Article ID 864605; 8 pages; (the year of publication is sufficiently earlier than the effective U.S. filing date and any foreign priority date so that the particular month of publication is not in issuee) 2011.

Vaso et al.; Peripheral nervous system origin of phantom limb pain; PAIN; 155(7); pp. 1384-1391; Jul. 1, 2014.

Waataja et al.; Effects of high-frequency alternating current on axonal conduction through the vagus nerve; J. Neural Eng.; 8(5); pp. 1-7; Sep. 15, 2011.

Ziegler-Graham et al.; Estimating the Prevalence of Limb Loss in the United States: 2005 to 2050; Arch Phys Med Rehabil; 89(3); pp. 422-429; Mar. 1, 2008.

\* cited by examiner

| GENERAL PARAMETERS | |
|---|---|
| WAVEFORM | SINUSOIDAL |
| FREQUENCY | 10 kHz |
| LOCKOUT | OFF |
| CHANNEL SEQUENCE: | A FIRST |
| CHANNEL DELAY: | 0 min |

FIG. 5A

TABLE 1.1a: TEST PARAMETER SETTINGS

| | | DOSE 1 | | DOSE 2 | |
|---|---|---|---|---|---|
| CHANNEL A | ENABLED | YES | ENABLED | NO |
| | INITIAL AMPLITUDE (Vp): | 0 | INITIAL AMPLITUDE (Vp): | - |
| | RAMP DURATION (min): | 15 | RAMP DURATION (min): | - |
| | FINAL AMPLITUDE (Vp): | 15 | FINAL AMPLITUDE (Vp): | - |
| | PLATEAU DURATION (min): | 15 | PLATEAU DURATION (min): | - |
| CHANNEL B | ENABLED | NO | ENABLED | NO |
| | INITIAL AMPLITUDE (Vp): | - | INITIAL AMPLITUDE (Vp): | - |
| | RAMP DURATION (min): | - | RAMP DURATION (min): | - |
| | FINAL AMPLITUDE (Vp): | - | FINAL AMPLITUDE (Vp): | - |
| | PLATEAU DURATION (min): | - | PLATEAU DURATION (min): | - |

FIG. 5B

TABLE 1.2a: TIME ELAPSED AND THERAPY INDUCED SENSATION DESCRIBED BY SUBJECT

| SENSATION DESCRIPTION | FIRST FELT (Abort if Time ≥ 5 min and repeat with 5 kHz) | STRONG | VERY STRONG | TOO STRONG Turn OFF Therapy! |
|---|---|---|---|---|
| TIME (min : sec) | : | : | : | : |
| SENSATION RATING ON NRS (0-10) | | | | |

FIG. 5C

TABLE 1.3: INITIAL AMPLITUDE BASED ON TIME WHEN INDUCED SENSATION WAS "FIRST FELT"

| INITIAL AMPLITUDE (Vp) | | SECONDS | | |
|---|---|---|---|---|
| | | 0-19 | 20-39 | 40-59 |
| MINUTES | 0 | 0.2 | 0.3 | 0.7 |
| | 1 | 1.0 | 1.3 | 1.7 |
| | 2 | 2.0 | 2.3 | 2.7 |
| | 3 | 3.0 | 3.3 | 3.7 |
| | 4 | 4.0 | 4.3 | 4.7 |

FIG. 5D a. DOSE 1

| FINAL AMPLITUDE (Vp) | SECONDS | | | | | |
|---|---|---|---|---|---|---|
| MINUTES | 0-9 | 10-19 | 20-29 | 30-39 | 40-49 | 50-59 |
| 0 | - | 1.6 | 2.3 | 2.8 | 3.3 | 3.7 |
| 1 | 4.0 | | 4.5 | | 5.0 | |
| 2 | 6.0 | | | 6.5 | | |
| 3 | 7.0 | | | 7.5 | | |
| 4 | 8.0 | | | 8.5 | | |
| 5 | 9.0 | | | | | |
| 6 | 10.0 | | | | | |
| 7 | 11.0 | | | | | |
| 8 | 12.0 | | | | | |
| 9 | 12.5 | | | | | |
| 10 | 13.0 | | | | | |
| 11 | 13.5 | | | | | |
| 12 | 14.0 | | | | | |
| 13 | 14.5 | | | | | |
| 14 | 15.0 | | | | | |
| 15 | 16.0 | | | | | |

FIG. 5E b. DOSE 2

| FINAL AMPLITUDE (Vp) | SECONDS | | | | | |
|---|---|---|---|---|---|---|
| MINUTES | 0-9 | 10-19 | 20-29 | 30-39 | 40-49 | 50-59 |
| 0 | - | 1.3 | 1.8 | 2.2 | 2.6 | 3.0 |
| 1 | 3.2 | | 3.6 | | 4.0 | |
| 2 | 4.5 | | | 5.0 | | |
| 3 | 5.5 | | | 6.0 | | |
| 4 | 6.5 | | | 7.0 | | |
| 5 | 7.5 | | | | | |
| 6 | 8.0 | | | | | |
| 7 | 8.5 | | | | | |
| 8 | 9.0 | | | | | |
| 9 | 9.5 | | | | | |
| 10 | 10.5 | | | | | |
| 11 | 11.0 | | | | | |
| 12 | 11.0 | | | | | |
| 13 | 11.5 | | | | | |
| 14 | 12.0 | | | | | |
| 15 | 13.0 | | | | | |

FIG. 5F

| GENERAL PARAMETERS | |
|---|---|
| WAVEFORM | SINUSOIDAL |
| FREQUENCY | 5 kHz / 10 kHz |
| LOCKOUT | 0.5 Hr |
| CHANNEL SEQUENCE: | A FIRST |
| CHANNEL DELAY: | 0 min |

FIG. 5G

TABLE 1.1b: FINAL PARAMETER SETTINGS

<table>
<tr><td colspan="2"></td><th colspan="2">DOSE 1</th><th colspan="2">DOSE 2</th></tr>
<tr><td rowspan="5">CHANNEL A</td><td>ENABLED</td><td>YES</td><td>ENABLED</td><td>YES</td></tr>
<tr><td>INITIAL AMPLITUDE (Vp):</td><td>(From Table 1.3)</td><td>INITIAL AMPLITUDE (Vp):</td><td>(From Table 1.3)</td></tr>
<tr><td>RAMP DURATION (min):</td><td>15</td><td>RAMP DURATION (min):</td><td>15</td></tr>
<tr><td>FINAL AMPLITUDE (Vp):</td><td>(From Table 1.4a)</td><td>FINAL AMPLITUDE (Vp):</td><td>(From Table 1.4b)</td></tr>
<tr><td>PLATEAU DURATION (min):</td><td>15</td><td>PLATEAU DURATION (min):</td><td>15</td></tr>
<tr><td rowspan="5">CHANNEL B</td><td>ENABLED</td><td>NO</td><td>ENABLED</td><td>NO</td></tr>
<tr><td>INITIAL AMPLITUDE (Vp):</td><td>-</td><td>INITIAL AMPLITUDE (Vp):</td><td>-</td></tr>
<tr><td>RAMP DURATION (min):</td><td>-</td><td>RAMP DURATION (min):</td><td>-</td></tr>
<tr><td>FINAL AMPLITUDE (Vp):</td><td>-</td><td>FINAL AMPLITUDE (Vp):</td><td>-</td></tr>
<tr><td>PLATEAU DURATION (min):</td><td>-</td><td>PLATEAU DURATION (min):</td><td>-</td></tr>
</table>

FIG. 5H

TABLE 2.1: FINAL AMPLITUDE ADJUSTMENT BASED ON INDUCED SENSATION DURING TEST

| SENSATION BY D1 | WEAK | STRONG | VERY STRONG | TOO STRONG |
|---|---|---|---|---|
| ADJUSTMENT | New = Current * 1.2† | New = Current | New = Current * 0.9† | New = Current * 0.8† |

† Suggested Factor, actual value to be determined with clinical experience and subject feedback

FIG. 6A

GENERAL PARAMETERS

| WAVEFORM | SINUSOIDAL |
|---|---|
| FREQUENCY | 5 kHz / 10 kHz |
| LOCKOUT | 0.5 Hr |
| CHANNEL SEQUENCE: | A FIRST |
| CHANNEL DELAY: | 0 min |

FIG. 6B

|   |   | DOSE 1 |   | DOSE 2 |   |
|---|---|---|---|---|---|
| CHANNEL A | ENABLED | YES |   | ENABLED | YES |
|   | INITIAL AMPLITUDE (Vp): | No Change |   | INITIAL AMPLITUDE (Vp): | No Change |
|   | RAMP DURATION (min): | 15 |   | RAMP DURATION (min): | 15 |
|   | FINAL AMPLITUDE (Vp): | New Value per Step 6 |   | FINAL AMPLITUDE (Vp): | D1 * 0.8 † |
|   | PLATEAU DURATION (min): | 15 |   | PLATEAU DURATION (min): | 15 |
| CHANNEL B | ENABLED | NO |   | ENABLED | NO |
|   | INITIAL AMPLITUDE (Vp): | - |   | INITIAL AMPLITUDE (Vp): | - |
|   | RAMP DURATION (min): | - |   | RAMP DURATION (min): | - |
|   | FINAL AMPLITUDE (Vp): | - |   | FINAL AMPLITUDE (Vp): | - |
|   | PLATEAU DURATION (min): | - |   | PLATEAU DURATION (min): | - |

FIG. 6C

APPARATUSES AND METHODS FOR SETTING AN ELECTRICAL DOSE

CROSS REFERENCE TO RELATED APPLICATIONS

This patent is a continuation of U.S. patent application Ser. No. 17/455,392, filed Nov. 17, 2021, titled "APPARATUSES AND METHODS FOR SETTING AN ELECTRICAL DOSE," now U.S. Patent Application Publication No. 2022/0072310, which is a continuation of U.S. patent application Ser. No. 16/379,053, filed on Apr. 9, 2019, titled "APPARATUSES AND METHODS FOR SETTING AN ELECTRICAL DOSE," now U.S. Pat. No. 11,213,682, which claims priority to U.S. Provisional Patent Application No. 62/655,122, filed on Apr. 9, 2018, titled "APPARATUSES AND METHODS FOR SETTING AN ELECTRICAL DOSE," each of which is herein incorporated by reference in its entirety.

This patent may be related to one or more of: U.S. patent application Ser. No. 15/510,824, titled "NERVE CUFF ELECTRODE FOR NEUROMODULATION IN LARGE HUMAN NERVE TRUNKS" and filed on Sep. 12, 2014, which claims priority to U.S. patent application Ser. No. 14/276,200 (now U.S. Pat. No. 8,983,612) filed May 13, 2014; which is a continuation of U.S. patent application Ser. No. 13/474,926 filed May 18, 2012 now U.S. Pat. No. 8,731,676; which claims priority to U.S. patent application Ser. No. 61/487,877 filed May 19, 2011, each of which is expressly incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The inventions described herein relate to the field of implantable neuromodulators.

BACKGROUND

Implantable neuromodulators (e.g., implantable neurostimulators) are increasingly used to treat pain and other indications, in many cases by the direct application of electrical energy to one or more nerves, including nerve bundles. Such electrical modulation may be used to excite or inhibit nerves, or both. An implantable neuromodulator may be implanted on, around or adjacent to a patient's nerve or nerves for the delivery of electrical energy.

For example, electrical modulation may be applied to a nerve to treat the unwanted and/or uncoordinated generation of nerve impulses which may otherwise be a disabling factor in some medical conditions. Uncoordinated motor signals may produce spasticity in stroke, cerebral palsy, multiple sclerosis, and other conditions and may lead to pain, including pain resulting from amputation. The uncoordinated signals may result in the inability to make desired functional movements. Involuntary motor signals in conditions including tics, choreas, and so on, may produce unwanted movements. Unwanted sensory signals can cause pain.

Electrical modulation to treat a patient is generally sensitive to the amount, during and intensity of the applied energy. For example, one non-limiting type of electrical therapy is applying high-frequency alternating current (HFAC) to nerves that has been shown to block nerve activity, e.g., in the treatment of pain. An appropriate dose (e.g., the amount of electrical energy applied to the patient for effective treatment) may be set so that it causes the desired effect, such as inhibition of nerve activity to reduce pain. On the other hand, an inappropriate dosing may lead to no effect or possibly to irritation of the nerve.

Unfortunately, determining proper dosing for a patient may be time-intensive, and complicated. Further, the optimal dosing to treat a patient may be highly variable between patients, and indeed, even over time in the same patient. Thus, it would be beneficial to provide a method and/or apparatus for simplifying and reliably setting patient dosing. Described herein are methods and apparatuses that may address these needs.

SUMMARY OF THE DISCLOSURE

Described herein are methods and apparatuses (devices, systems, etc., including neuromodulators and systems including them) for setting the therapeutic dosing of a neuromodulator that is implanted into a patient. A therapy dose typically includes a therapeutic dose duration including a therapy ramp-up time to reach a peak modulation voltage and a sustained peak modulation time during which the voltage is sustained at the peak modulation voltage. The setting processes described herein may adjust (e.g., set) the peak voltage of ramp to a voltage that is beyond the patient's nerve activation level and within a nerve blocking level. The dose parameters may also include the waveform parameters applied, e.g., pulsatile or repeating (e.g., sinusoidal, square wave, saw-tooth, biphasic, etc.), and the frequency of the applied waveform (e.g., the high-frequency component). Other dose parameters may include the initial (e.g., starting) voltage, which may be, e.g., zero, or may be a minimum patient-detectable modulation voltage that is determined as described herein. In some variations, the therapeutic dose includes at last two parts; an initial ramp-up portion in which the voltage increases from the initial voltage up to a peak modulation voltage, and a plateau portion, referred to as a sustained peak modulation time, during which the voltage is sustained at the peak modulation voltage. The duration of the ramp-up portion may be referred to as the ramp-up time. The duration of the second portion may be referred to as the plateau time. In some variations, these two portions may repeat and/or alternate.

The methods and apparatuses described herein may use a testing ramp applied by the implanted neuromodulator to identify a peak modulation voltage that is patient-specific and provides that patient with a maximal therapeutic effect while remaining comfortably tolerable by the patient during the application of energy by the neuromodulator. The testing ramp may be applied as part of a therapy dose-setting procedure during which a ramped voltage, having the same or a similar frequency as the therapeutic dose will have, is applied by the implanted neuromodulator. Feedback, either direct (such as patient reporting) or indirect (e.g., from patient biometrics) or both may be used to select the target sensation intensity modulation voltage. The target sensation intensity modulation voltage identified during the testing ramp application may be used, along with the intended therapeutic ramp-up time to determine the therapeutic dose peak modulation voltage. Thus, the methods and apparatuses described herein may, using a single test including a ramp-up in voltage intensity, determine an optimal dosage.

In the absence of the teachings described herein, it is difficult to determine an optimal dosage at which the applied voltage is increase to a peak and sustained for sufficiently long to achieve a therapeutic benefit. The inventors have found that although it is generally beneficial to apply as high a voltage as possible to the patient, particularly (but not exclusively) in applications in which neural modulation comprises high-frequency (e.g., greater than 1 kHz) modulation from an implanted neuromodulator to inhibit activity of a nerve or nerve bundle, there is a difficulty to define voltage threshold, above which further voltage amplitude may result in pain and/or discomfort for the patient. This threshold is not only variable between different patients, but may vary with respect to the individual patient. For example, patient sensitivity appears to depend at least slightly on the rate of increase of the voltage. Slower ramp-up times may generally permit a higher final voltage. However, inventors have also found that it is beneficial to maintain the therapeutic modulation such that a longer time is spent at the maximum voltages (e.g., the sustained or plateau period). Surprisingly, the inventors have found that it is possible to use a target sensation intensity modulation voltage that is specific to the patient from the test voltage ramp and scale this target sensation intensity modulation voltage for other ramps, which may allow for the use of a single setting (e.g., therapy dose-setting) procedure to determine the target sensation intensity modulation voltage from a known ramp-up to be used to determine a therapeutic peak modulation voltage, as described in detail herein.

Note that the target sensation intensity modulation voltage may be the voltage that induces a target intensity of sensation in the patient during the test. More specifically, this target sensation intensity modulation voltage may be the maximum voltage that the patient can tolerate for the therapy period.

In any of the methods described herein, the testing may be performed on a patient after a period of inactivity (non-modulation) of the neuromodulator device. For example, there may be a recovery period during which the maximum voltage to induce the target intensity of sensation may change, and be unreliable. Thus, the method may have a delay period before applying the test ramp. This delay may be 1 minute or more, 5 minutes or more, 10 minutes or more, 15 minutes or more, 20 minutes or more, 25 minutes or more, 30 minutes or more, 35 minutes or more, 40 minutes or more, 1 hour or more, etc. The testing period may itself be brief (e.g., one or more trials of 30 min or less, which may be separated by this delay period).

In general these methods may be applied to, but are not limited to, the use with neuromodulation to provide a high-frequency block of a nerve or bundle of nerves. For example, these methods and apparatuses may be used to set and/or optimize therapy treatment dosing for a high-frequency block of a nerve such as the sciatic nerve, dorsal root ganglion (DRG), etc.

For example, described herein are methods of setting a therapeutic dose of a neuromodulator implanted into a patient, wherein the therapeutic dose comprises a therapeutic dose duration including a therapy ramp-up time to reach a peak modulation voltage and a sustained peak modulation time during which the voltage is sustained at the peak modulation voltage. The method may include: applying a test voltage ramp from the neuromodulator implanted into the patient; determining a target sensation intensity modulation voltage that is specific to the patient from the test voltage ramp; estimating the peak modulation voltage as a function of the target sensation intensity modulation voltage and the therapy ramp-up time to reach the peak modulation voltage; and setting the therapeutic dose using the estimated peak modulation voltage.

The target sensation intensity modulation voltage may be a maximum patient-tolerable modulation voltage.

In general, the therapy ramp-up time may be any appropriate portion of the therapeutic dose duration, such as between about 10% and about 90% (e.g., between about 30% and about 70%, between about 40% and about 60%, between about 45% and about 55%, about 50%, etc.). For example, the therapy ramp-up time to the peak modulation voltage may be set to be half of the therapeutic dose duration. The balance of the therapeutic dose duration may be the plateau period (e.g., the sustained peak modulation time). As mentioned, above, in some variations, the therapeutic dose may then repeat, either immediately or more preferably after a "lockout" period during which modulation is not applied by the neuromodulator. The lockout period may be 5 minutes or more (e.g., 5 minutes, 10 minutes, 15 minutes, 20 minutes, 25 minutes, 30 minutes, 35 minutes, 40 minutes, 45 minutes, 50 minutes, 55 minutes, 60 minutes, etc.).

The therapeutic dose duration may be any appropriate length of time, e.g., between about 5 minutes and about 2 hours, e.g., between about 10 minutes and 1 hours, between about 15 minutes and 50 minutes, between about 20 minutes and 45 minutes, between about 25 minutes and about 40 minutes, etc., such as about 30 minutes.

Determining the target sensation intensity modulation voltage may include determining the voltage of the test voltage ramp being applied when a patient-reported feedback indicating the strongest sensation that the patient can tolerate for a therapeutic dose is received during the application of the test voltage ramp. During the application of the voltage ramp, for example, the patient may self-report on the experienced sensation from the applied voltage ramp. In particular, the patient may report (verbally, by activating a control such as a button, touchscreen, etc.) that the sensation is first felt and/or barely noticeable, and/or when the sensation is strong (e.g., "strong but does not bother me") and/or very strong (e.g., the "strongest sensation I can tolerate for the treatment period").

In general, estimating the peak modulation voltage as a function of the target sensation intensity modulation voltage and therapy ramp-up time may include estimating the peak modulation voltage as a product of a function of the therapy ramp-up time and a function of the target sensation intensity modulation voltage. For example, estimating the peak modulation voltage as a function of the target sensation intensity modulation voltage and therapy ramp-up time may comprise estimating the peak modulation voltage as a square root of a product of the therapy ramp-up time and the target sensation intensity modulation voltage.

Any of these methods may also include determining a minimum patient-detectable modulation voltage that is specific to the patient from the test voltage ramp and further wherein setting the therapeutic dose comprises using the minimum patient-detectable modulation voltage as a starting voltage for the therapeutic dose. For example, determining the minimum patient-detectable modulation voltage may include receiving patient reported feedback during the application of the test voltage ramp, as mentioned above.

In general, setting the therapeutic dose may include setting the therapeutic dose in the implanted neuromodulator or a controller in communication with the implanted neuromodulator. Setting the therapeutic dose may also include setting one or more of: the therapeutic dose duration, the therapy ramp-up time to reach the peak modulation voltage, and the sustained peak modulation time. These parameters may be set for the test voltage ramp.

In general, the applied therapeutic energy may include a high-frequency modulation signal (waveform) that is ramped up to a plateau value. As mentioned above, any of these methods may also include setting the frequency of the high-frequency component of the test voltage ramp applied and setting a frequency of the high-frequency component of the therapeutic dose to the frequency of the high-frequency component of the test voltage ramp applied. For example, the frequency of the high-frequency component of the test voltage ramp applied may be between 1 kHz and 100 kHz.

Any of these methods may also include setting an alternative therapeutic dose of the neuromodulator implanted into a patient. The alternative therapeutic dose may comprise an alternative peak modulation voltage that is between about 60% and 95% of the peak modulation voltage. The alternative therapy dose may be provided to allow the patient to apply one or the other therapy doses (the therapy dose or the alternative therapy dose) at their preference.

For example, a method of setting a therapeutic dose of a neuromodulator implanted into a patient, wherein the therapeutic dose comprises a therapeutic dose duration including a therapy ramp-up time to reach a peak modulation voltage and a sustained peak modulation time during which the voltage is sustained at the peak modulation voltage, may include: applying a test voltage ramp from the neuromodulator implanted into the patient; determining a minimum patient-detectable modulation voltage that is specific to the patient from the test voltage ramp; determining a target sensation intensity modulation voltage that is specific to the patient from the test voltage ramp; estimating the peak modulation voltage as a product of a function of the target sensation intensity modulation voltage and a function of the therapy ramp-up time to reach the peak modulation voltage; and setting the therapeutic dose using the estimated peak modulation voltage and using the minimum patient-detectable modulation voltage as a starting voltage for the therapeutic dose.

Also described herein are systems that are configured to implement any of the methods described herein either automatically or semi-automatically. For example, a system may include: an implantable neuromodulator; a controller for controlling the application of a therapeutic dose by the neuromodulator, wherein the therapeutic dose comprises a therapeutic dose duration including a therapy ramp-up time to reach a peak modulation voltage and a sustained peak modulation time during which the voltage is sustained at the peak modulation voltage, the controller comprising one or more processors; memory coupled to the one or more processors, the memory configured to store computer-program instructions, that, when executed by the one or more processors, implement a computer-implemented method, the computer-implemented method comprising: applying a test voltage ramp from the neuromodulator implanted into the patient; determining a target sensation intensity modulation voltage that is specific to the patient from the test voltage ramp; estimating the peak modulation voltage as a function of the target sensation intensity modulation voltage and the therapy ramp-up time to reach the peak modulation voltage; and setting the therapeutic dose using the estimated peak modulation voltage.

The computer-implemented method may include any of the steps described above, which may be implemented by the controller. For example, when determining a target sensation intensity modulation voltage that is specific to the patient from the test voltage ramp, the controller may prompt the patient or otherwise allow the patient to enter their reported sensation induced by the ongoing modulation.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-5H are tables that may be used to determine a therapeutic dose. FIGS. 5A-5H include test parameter setting (FIGS. 5A and 5B), time elapsed and therapy induced sensation described by subject (FIG. 5C), initial amplitude based on time when induced sensation was "first felt" (FIG. 5D), look-up tables to determine final amplitude (Vp) based on the strength of the induced sensation (FIG. 5E) and a discounted final amplitude for a second, alternative, dose (FIG. 5F).

DETAILED DESCRIPTION

In general, the methods and apparatuses for performing them described herein allow optimized dose setting of a neuromodulation apparatus so that the therapy dose provided by the neuromodulator maximizes the energy which may enhance the effect of the neuromodulation on the target nerve(s) without irritating or harming the patient. These methods and apparatuses may be generally described for use with an implanted neuromodulator, but may be also or alternatively be used with external neuromodulators or neuromodulators prior to implantation. Further, the examples provided herein are provided in reference to neuromodulatory inhibition by the application of high-frequency neuromodulation, however these methods and apparatuses may also be used with other neurostimulatory regimes including general neuromodulation. Examples of neuromodulator apparatuses and methods that may benefit from these methods and apparatuses may include, for example, spinal cord stimulators (SCS) and any other neuromodulation application that may be improved by the optimization between therapeutic benefit and induced sensation.

The inventors have generally found that increasing the applied voltage of neuromodulation is beneficial, particularly when sustained at a high voltage (e.g., high peak voltage). However, high voltage neuromodulation applied to a patient's nerve may result in pain and discomfort when the modulation exceeds a threshold voltage during the ramp up to the sustained high voltage. The value of this threshold may vary between patients and also appears to vary based on the recent modulation already experienced by the nerve as well as the modulation parameters (e.g., frequency). In general, a slower ramp up to a peak modulation voltage in a therapeutic dose may result in lower intensities of induced sensation, and therefore correspondingly higher peak modulation voltages. However, it is also beneficial for a therapeutic dose to maintain the peak modulation voltage for as long as possible during the therapeutic dose.

Described herein are methods of determining a target sensation intensity modulation voltage using a generic test ramp and adapting this target intensity of modulation to determine an optimal peak modulation voltage for neuromodulation.

Figure 1:
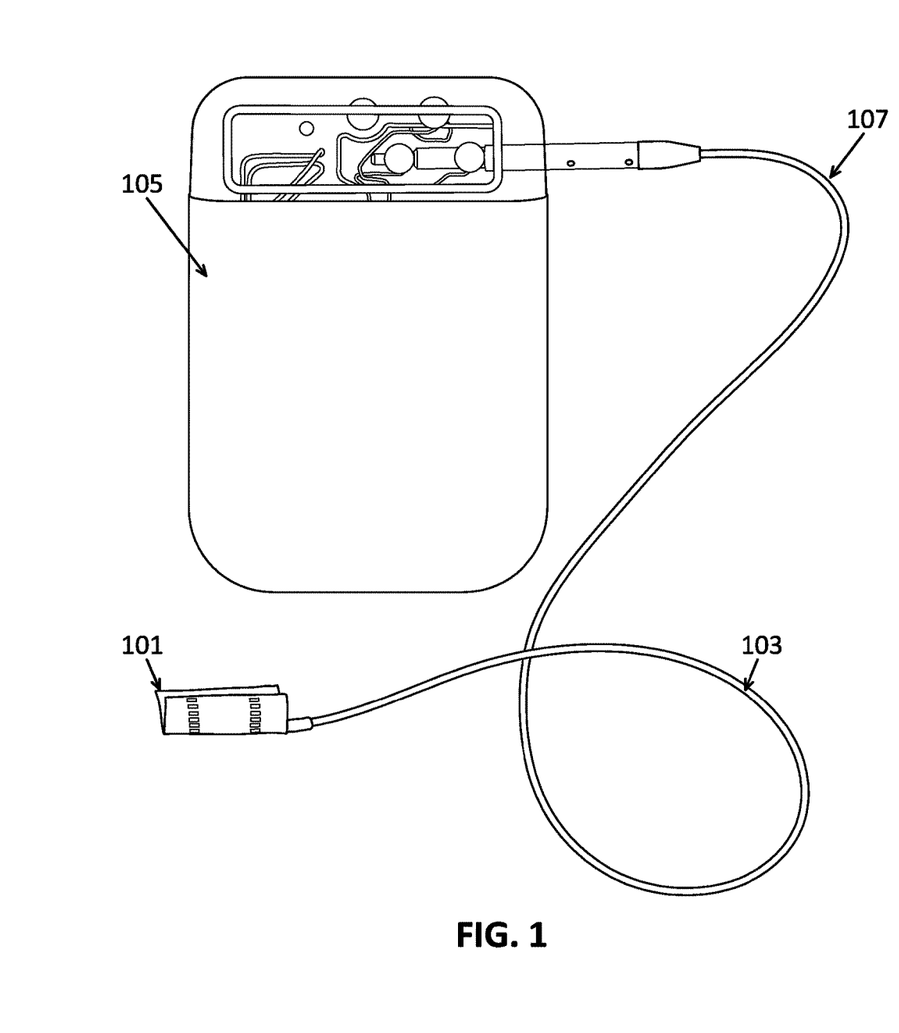
FIG. 1 shows one example of a neuromodulation system (showing a nerve cuff, lead and implantable controller/waveform generator).

These methods and apparatuses may be used with any appropriate neuromodulator. FIG. 1 illustrates one example of an implantable neuromodulator including a nerve cuff 101, a lead 103 connecting the nerve cuff to a controller (e.g., waveform generator, control circuitry, power source, communications circuitry and/or antenna, etc.) 105. Systems including a nerve cuff such as those described herein, may be used, for example, to apply a high frequency nerve block to acutely treat pain, either acute pain or chronic pain (more than 6 months in duration), in humans by blocking nerve conduction on an action potential. Acute treatment may refer to on-demand treatment with substantially immediate pain relief effect. The nerve cuff may be applied onto a moderate and relatively large diameter nerves such as the sciatic nerve. One therapy involves reversibly blocking peripheral nerves by applying high frequency alternating current directly on a nerve trunk. Specifically, a current ranging from 1 kHz to 100 kHz (e.g., 5 kHz to 50 kHz) may be applied; this may be referred to as a high frequency modulation, compared to a current of less than 1 kHz applied in the conventional electrical modulation described above. Efficacy of the high frequency alternating current therapy in acute non-human animal experiments (frog, cat) has been reported. U.S. Pat. Nos. 7,389,145 and 8,060,208 describe in general this electrical modulation technology.

The nerve cuffs may encircle a particular segment of a targeted peripheral nerve, e.g., a sciatic nerve, a tibial nerve, etc. Using an implanted electrode connected to an electrical waveform generator, an electrical waveform may be applied for a time interval, e.g., 10 min (15 min, 20 min, 25 min, 30 min, 35 min, 40 min, etc.), sufficient to effect substantially immediate patient pain relief, e.g., within 10 min, and an extended period of pain relief up to several hours. The current may range, for example, from 4 mApp to 26 mApp.

The application of 10 kHz alternating current generated by a custom generator via a custom implanted nerve electrode may significantly reduce pain in the majority of patients treated. For example, an implantable electrode operatively connected to an external or implanted waveform generator may be used. The electrode may be a spiral cuff electrode similar to that described in U.S. Pat. No. 4,602,624. The electrode may be implanted in a human mammal on a desired peripheral nerve trunk proximal to the pain source (e.g., a neuroma), such that the cuff encircled the desired peripheral nerve in which the action potential was to be blocked. The cuff inner diameter may range from about 4 mm to about 13 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

Figure 2:
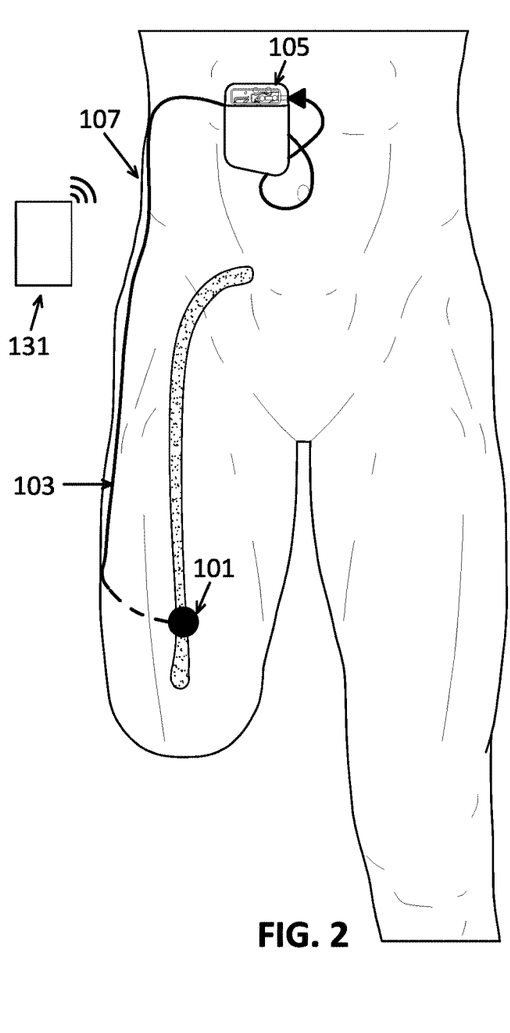
FIG. 2 shows an example of the system of FIG. 1 implanted into a patient (also showing a controller (in this example, an external controller) for controlling and applying a therapeutic dose.

For example, FIG. 2 illustrates the use of a system including a cuff electrode applied to the sciatic nerve of an amputee patient. In this example, the amputee 107 has been implanted with a nerve cuff 101 around the sciatic nerve (nerve trunk), and is connected, via a lead 103, to the controller including the waveform generator 105. This procedure may be done, for example, by first dissecting to expose the nerve in an open procedure, then wrapping the nerve with the flexible (self-closing) cuff. Once implanted the controller/waveform generator may be placed in a pocket in the anterorlateral abdominal wall, and a tunneling electrode cable may be positioned along the midaxilalary line (including transversely across the abdomen) to connect the controller/waveform generator to the nerve cuff electrode. Once the impedance of the nerve cuff is checked (e.g., by the controller) the incisions may be closed. The incision for implanting the nerve cuff is typically larger than about 1.5 inches (e.g., between 1.5 and 3 inches), so that sufficient visualization and access may be achieved. Once implanted and allowed to heal, the implanted neuromodulator may be set as described herein to provide an optimized therapeutic dose as described herein.

The system shown in FIG. 2 also includes a controller 131, shown as an external controller that include one or more processors and may be configured to perform the methods described herein. The controller, or a separate device coupled to the controller, may include an input for the user to report the sensation induced by the applied modulation, including the test ramp, as will be described in greater detail below.

Figure 3A:
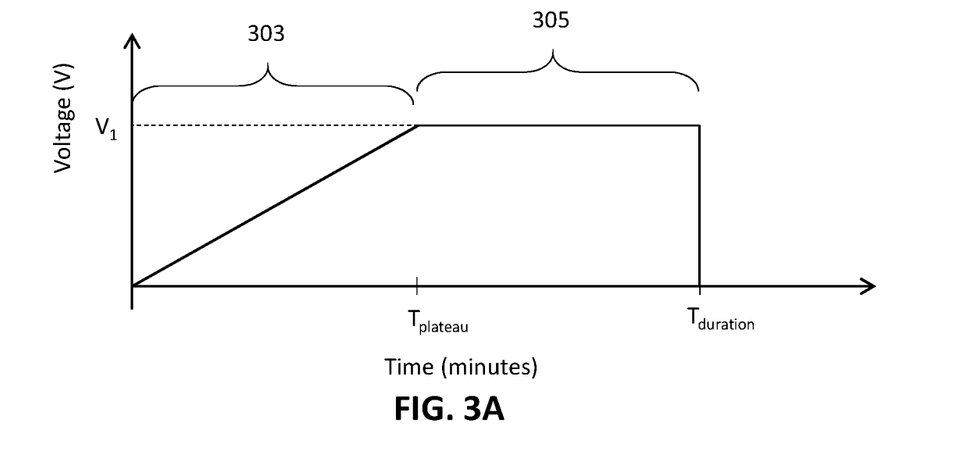
FIG. 3A is an example of a schematic of a voltage profile of a therapeutic dose.

In general a therapeutic dose for a neuromodulator may have at least two portions. FIG. 3A illustrates one example of an exemplary voltage profile of a therapeutic dose. In this example, the first portion of the therapeutic dose is a ramp-up period 303, which has a duration (referred to as a therapy ramp-up time to reach a peak modulation voltage, $V_1$ in FIG. 3A) of $T_{plateau}$ that is between 10% and 90% of the total duration of the therapeutic dose ($T_{duration}$). The second portion of the therapeutic dose is a sustained peak modulation time 305 during which the voltage is sustained at the peak modulation voltage ($V_1$), this may also be referred to as the plateau portion.

During the ramp-up portion of the therapeutic dose, the neuromodulator may apply an increasing intensity of modulation from the start (time 0, $T_0$) to the peak modulation voltage ($V_1$) at time $T_{plateau}$. In FIG. 3A this ramp period is shown as a linear increase, however it may increase in steps (e.g., incrementally increase following regular interval, such as increasing by 0.5 V every 30 seconds, etc.). In practice, the modulation may be applied with a high-frequency component having a frequency of between about 1 kHz and 100 kHz (e.g., 1 kHz and 50 kHz, 1 kHz and 40 kHz, 1 kHz and 30 kHz, 1 kHz and 25 kHz, about 5 kHz, about 10 kHz, etc.).

Figure 3B:
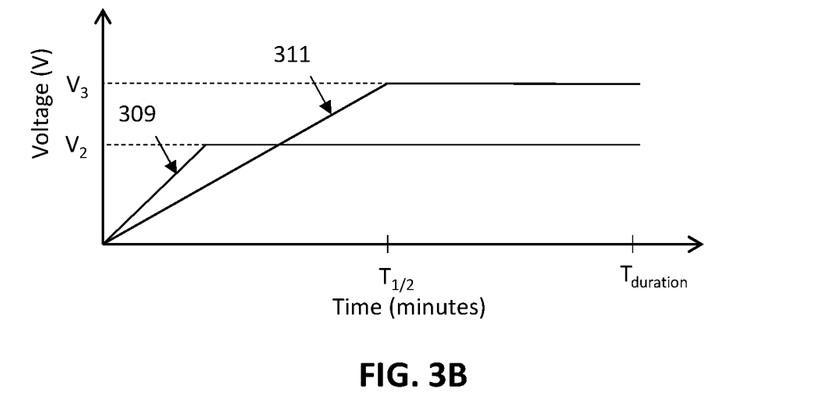
FIG. 3B illustrates examples a schematic of the voltage profiles of two therapeutic doses that may be applied by an implanted neuromodulator as described herein.
Figure 3C:
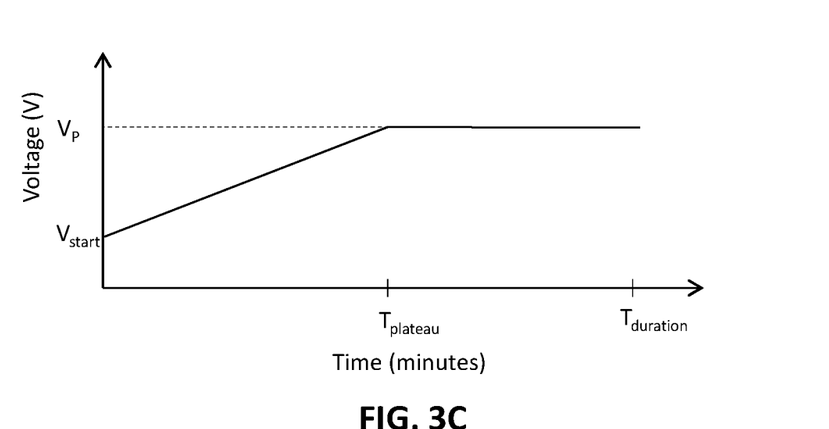
FIG. 3C illustrates another example of a voltage profile of a therapeutic dose.
Figure 4:
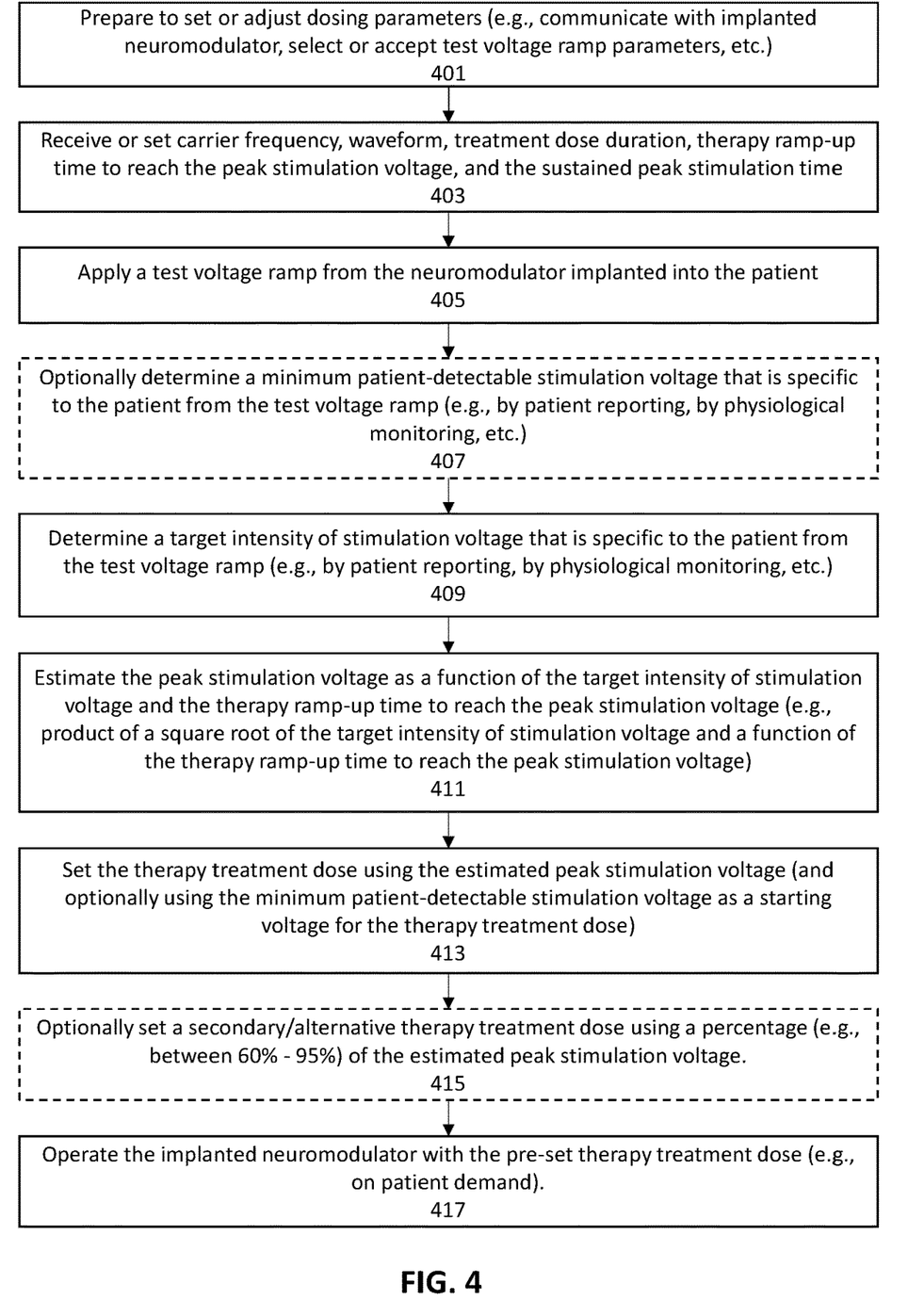
FIG. 4 is a flow diagram illustrating one method of setting a therapeutic dose for an implantable neuromodulator as described herein.

FIG. 3B illustrates another example of a pair of therapeutic dose profiles. In one example 309, a rapid ramp up reaches a first voltage level ($V_2$), and is held at this first voltage level for the duration of the dose. This first voltage level may result in a first sensation intensity for the patient, including a sensation intensity that is the maximum sensation that can be tolerated for the dose. The second profile 311 shows an example in which an approximately equivalent sensation intensity for the patient may be experienced, but with a much high voltage ($V_3$) that is reached by ramping up over a longer time period (shown as $T_{1/2}$, approximately half of the duration of the dose, $T_{duration}$). In this example, although the time at which the modulation applied is at the maximum peak voltage is longer for the first profile, the second profile has a much higher maximum peak voltage. In practice, once a maximum peak voltage is determined, a dose profile may be set for the neuromodulator by using a starting voltage (which may be determined from the minimum patient-detectable modulation voltage detectable by the patient) the peak modulation voltage (which may be determined as described herein) the ramp-up time to reach the peak modulation voltage, and either or both the total duration of the dose and/or the plateau duration, or equivalent values from which these values may be derived. The ramp-up time to reach the peak modulation voltage may be expressed as a time, or as a rate of voltage increase. The therapeutic dose may also include the waveform parameters to be applied (e.g., pulsed, such as sinusoidal), and the high-frequency component (e.g., between 1 kHz and 100 kHz, between 1 kHz and 50 kHz, e.g., about 5 kHz, about 10 kHz, etc.), etc.

In general, the maximum peak voltage may be determined empirically for any patient by applying a test ramp. The test ramp is a test voltage ramp from the neuromodulator implanted into the patient. While applying the test ramp, the patient may be interrogated (either manually or automatically) to determine the intensity experienced by the patient from the modulation. In particular, the patient may be interrogated to determine the first point at which the modulation becomes either noticeable or consistently perceived (e.g., a minimum patient-detectable modulation voltage). In some variations, this value may be used as the starting voltage during the therapeutic dose. The patient may also be interrogated to determine the target sensation intensity modulation voltage to be applied during the therapy dose. In some variations, this may be the maximum patient-tolerable modulation voltage.

The patient may be interrogated by prompting and/or receiving patient self-reported sensations. These sensations may be ranked (e.g., 1, corresponding to "I just started to feel the therapy;" 2, corresponding to "I only notice it when I pay attention to it;" 3, corresponding to "strong sensation but it doesn't bother me;" 4, corresponding to "strongest sensation that I can tolerate for 15-20 min;" and 5, corresponding to "I cannot tolerate this sensation for longer than a few minutes"). The apparatus may include an input that receives the patient intensity reporting and correlates intensity input to the applied voltage and/or the time during which the intensity was reported (which is equivalent information).

Alternatively, in some variations the apparatus may interrogate the patient indirectly, by monitoring patient biometric information (heart rate, pulse, blood pressure, ensemble nerve activity, skin conductance, respiration, biomarker, including pain biomarker, levels, etc.) that may also be correlated with this applied ramp to determine a target sensation intensity modulation voltage, including a maximum patient-tolerable modulation voltage.

Based on the identified voltage of the target sensation intensity from the applied test ramp, the method and/or apparatus may determine a target sensation intensity modulation voltage that is specific to the patient. This target sensation intensity modulation voltage (e.g., $V_s$) may then be used to calculate, e.g., estimate, the peak modulation voltage ($V_p$) in conjunction with the intendent therapy ramp-up time to reach this peak modulation voltage ($T_p$). Although the intended ramp-up time may be set to different values (typically between 10% and 90% of the total duration of the therapeutic dose), it may be set to, for example, half of the duration of the therapeutic dose (e.g., $T_{1/2}$). For example, the peak voltage may be set to be:

$$V_p = \sqrt{(T_p \times V_s)} = \sqrt{(T_p \times T_s \times R_s)} \quad (1)$$

As mentioned, $V_s$ is the voltage of the target sensation intensity determined by from the test ramp, $T_p$ is the ramp up time to get to the peak voltage, and $R_s$ is the ramp rate used during the test (since $T_s \times R_s$ is equivalent to $V_s$).

In some cases, where it is assumed that the duration of a therapeutic dose will be approximately 30 minutes, a 15 minute ramp-up time will result in an approximation for the Vp from the identified $V_s$ of:

$$Vp = 4 * \sqrt{V_s} \quad (2)$$

An example of this method is provided below, and shown in corresponding FIGS. 5A-6E.

EXAMPLE

Figure 5A:
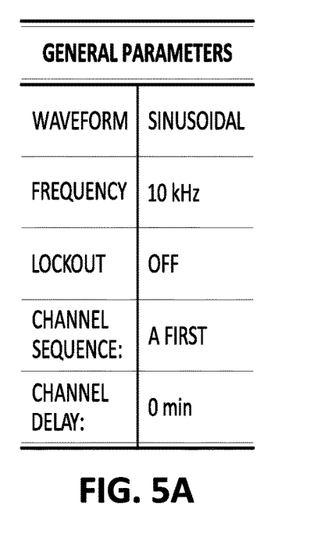
Figure 5B:
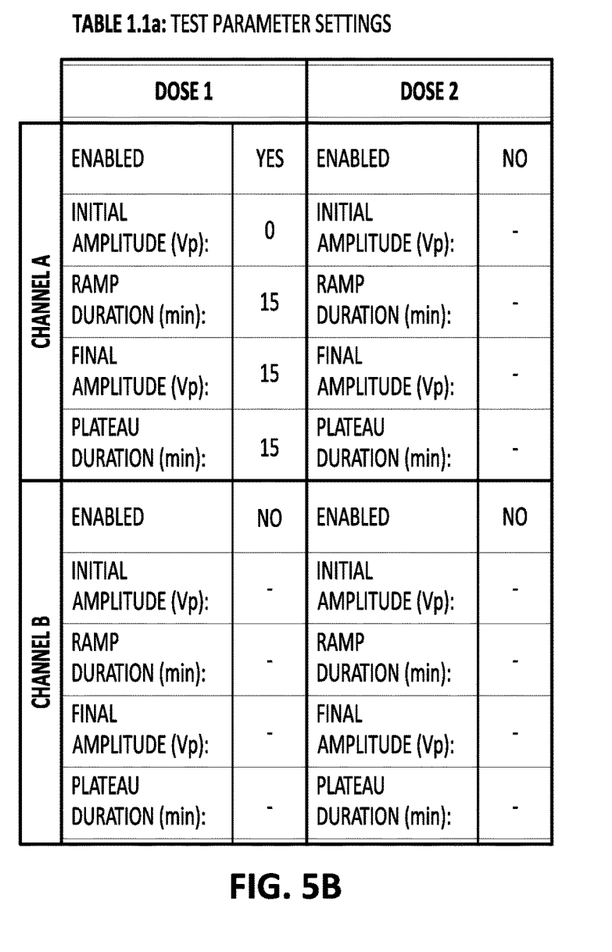
Figure 5C:
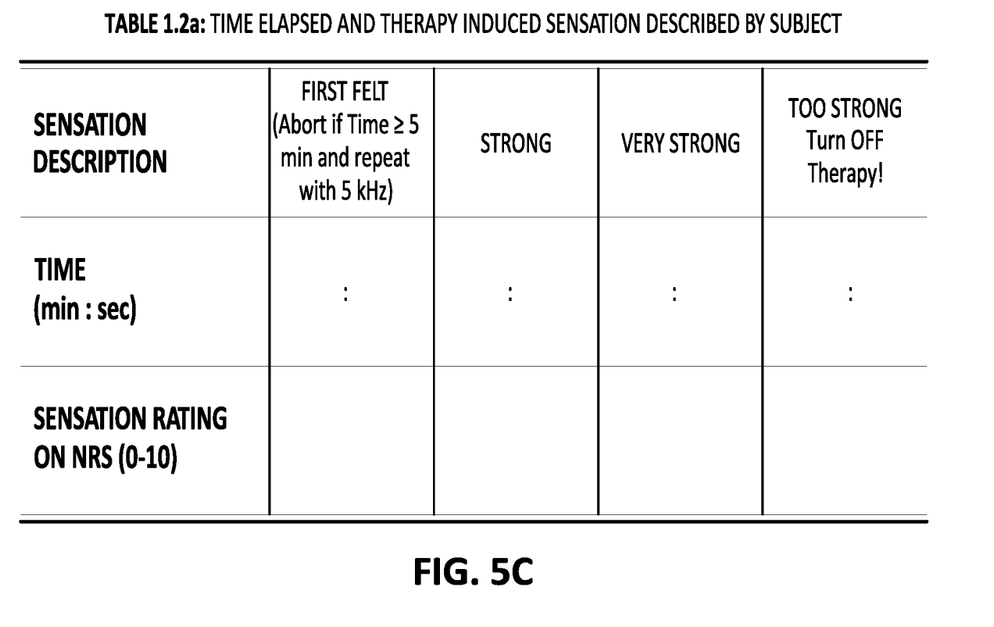

In one example, a maximum tolerable therapy voltage for each nerve was determined using the method described above. The implanted apparatus was similar to that shown in FIGS. 1 and 2. Patients for which an implantable neuromodulator was implanted were allowed to heal, and then trained to report sensations induced by modulation as:

First felt—"I just started to feel the therapy"
Weak—"I only notice it when I pay attention to it"
Strong—"Strong sensation but it doesn't bother me"
Very Strong—"Strongest sensation that I can tolerate for 15-20 min"
Too Strong—"I cannot tolerate this sensation for longer than a few minutes General set (e.g., pre-set) parameters for test as shown in FIG. 5A. FIG. 5B is a table illustrating the test parameter settings for the implanted apparatus. In this device, the two doses (dose 1 and dose 1), and two channels (channel A and channel B) are available. In FIG. 5B, only one (dose 1, channel A) is used ("enabled"). As shown in FIG. 5A, the general parameters include a sinusoidal waveform shape having a frequency of 10 kHz, and an initial amplitude (Vp) or 0 V. The initial ramp duration is intended to be 15 minutes plateau duration is 15 min (so the total dose duration is 30 min).

Figure 5D:
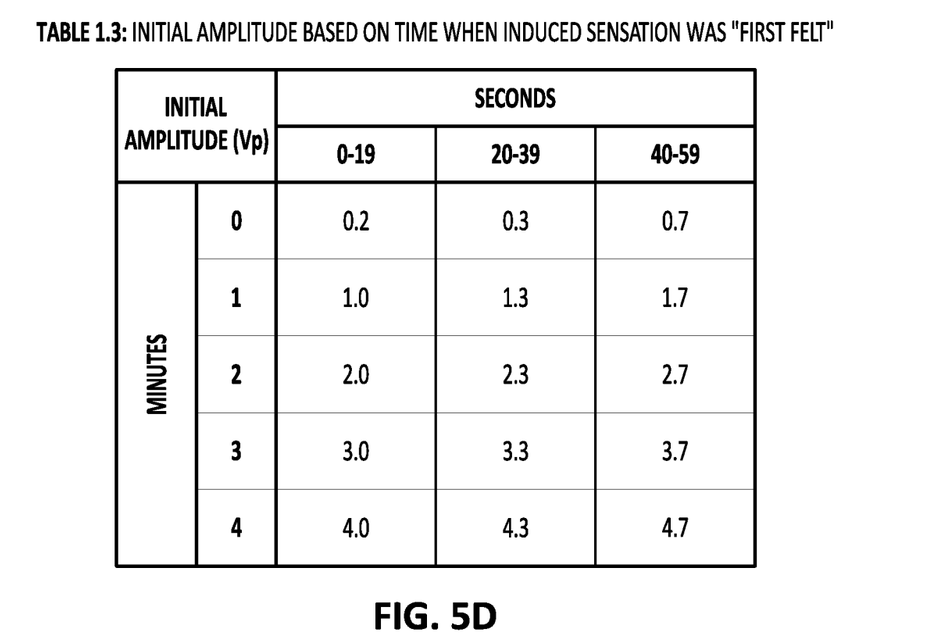

The test is started by simultaneously starting a clock and starting dose 1. The time is recorded along with the patient-reported induced sensation strength on NRS (e.g., in this example, in table 1.2a shown in FIG. 5C) for each sensation level. In this example, this sensation may most likely be a tingle or numbness on the medial side or foot of the phantom limb for these patients. If no sensation is felt in <5 min, abort test by clicking on "Stop Therapy" button and repeat with a different frequency (e.g., 5 kHz) after a rest period (e.g., 15 min of rest) to allow nerve recovery. Pilot study data indicated that similar therapeutic effects can be achieved at lower amplitudes by using a 5 kHz signal. When subject reports induced sensation as "Too strong", the therapy may be turned OFF by clicking on "Stop Therapy" button. The time may be recorded (e.g., in Table 1.2a) as well as the subject reported NRS rating of induced sensation Based on the time and therefore the voltage at which the sensation was first felt, a minimum patient-detectable modulation voltage that is specific to the patient from the test voltage ramp may be determined. Table 1.3 (FIG. 5D)

provide a simplified look-up table to convert the reported time into the minimum patient-detectable modulation voltage. For example, by identifying an initial amplitude corresponding to this value on Table 1.3, corresponding to "First felt" time (e.g., for a first felt time of 01:18, the value is 1.0 V).

Figure 5E:
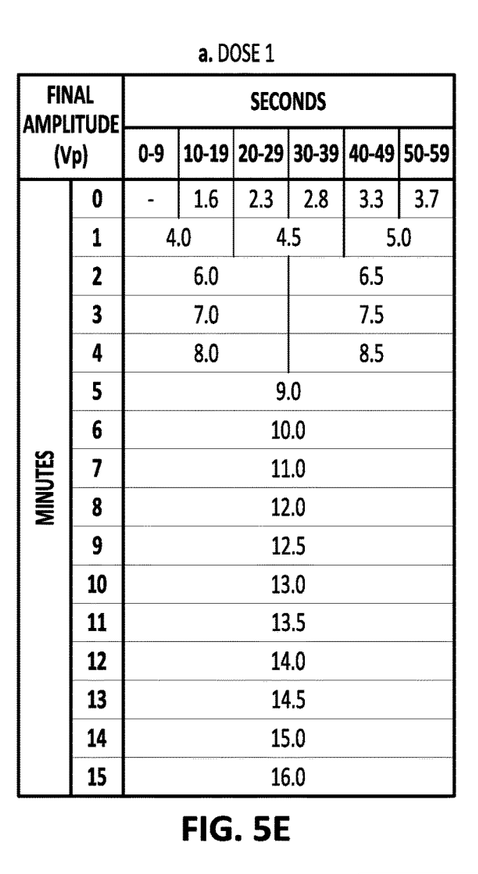
Figure 5F:
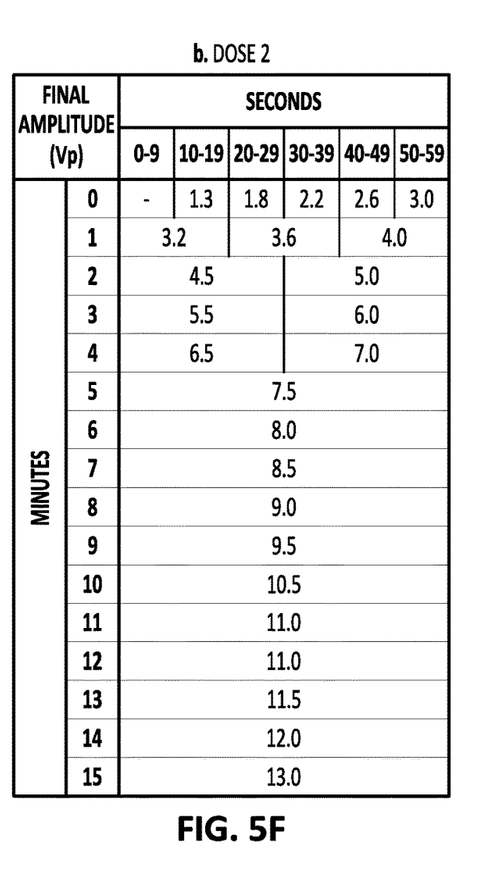

Similarly, the target sensation intensity modulation voltage that is specific to the patient may be determined from the test voltage ramp data. FIGS. 5E and 5F provide look-up tables that may be used to estimate the peak modulation voltage as a function of the target sensation intensity modulation voltage and the therapy ramp-up time to reach the peak modulation voltage, where the therapy ramp-up time is assumed to be 15 minutes (e.g., half of a 30 minute dose). In this example, the final amplitudes for dose may be identified from table 1.4a (FIG. 5E). Alternatively equation (1), above, may be used. In this example, the reported intensity corresponding to "Too Strong" time (e.g., for a "Too Strong" time of 07:35, the indicated value is 11.0 V) may be used to indicate the target sensation intensity modulation voltage.

FIG. 5F and table 1.4b provide a second, scaled peak amplitude that is 0.8× the value determined from Equation 1 and table 1.4a. This second dose may be provided as an alternative dose.

Figure 5G:
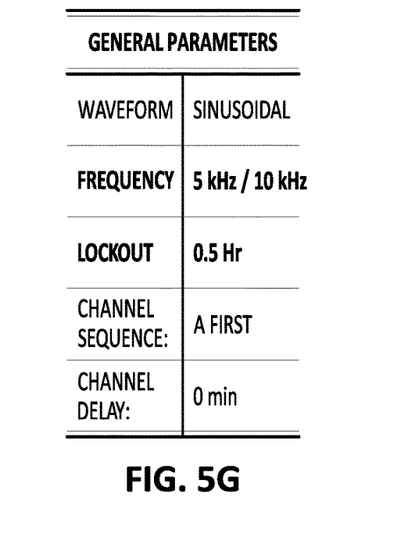
FIGS. 5G and 5H are tables illustrating test parameters, including the final parameter settings determined from FIGS. 5A-5G.
Figure 5H:
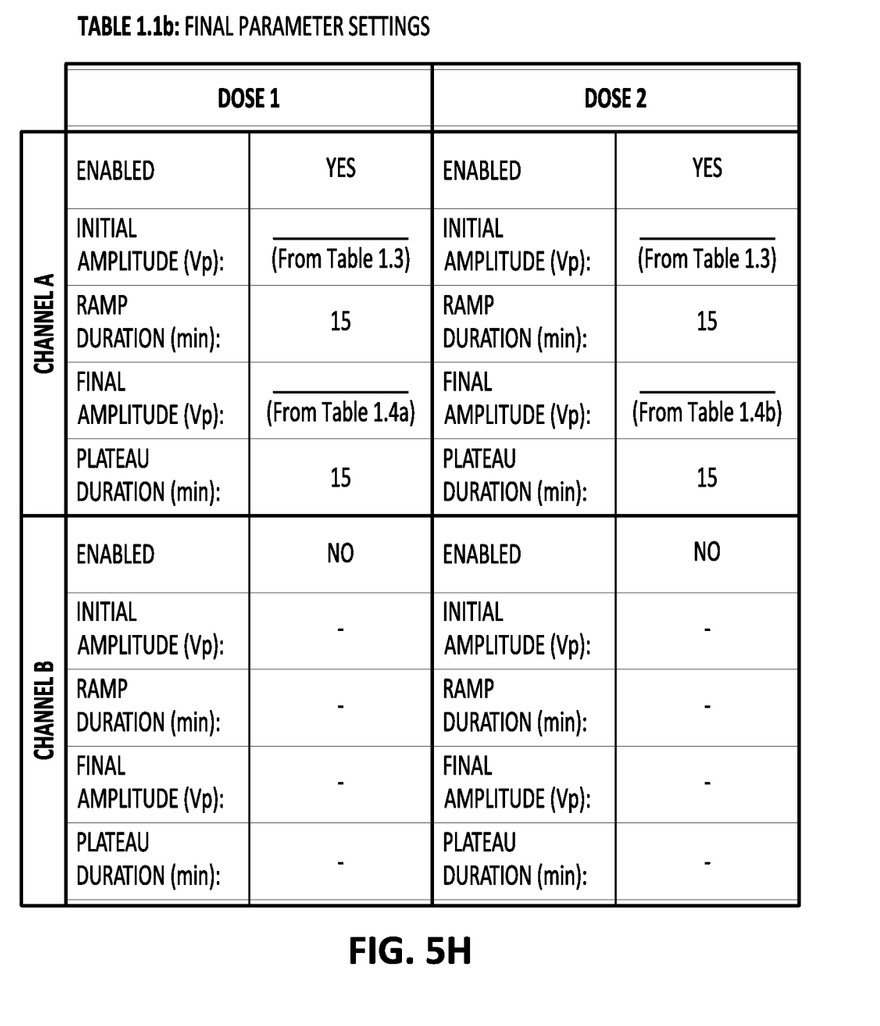

FIGS. 5G and 5H (table 1.1b) illustrate the final parameter settings for the therapeutic dose determined as described above. In this example, the general parameters may be as indicated in FIG. 5G, and the final parameter setts may be entered into the table 1.1b shown in FIG. 5H. For example, the initial amplitude may be entered into the table based on the minimum patient-detectable modulation voltage determined above. The final amplitude identified (e.g., using Table 1.4a and Table 1.4b in FIGS. 5E and 5F) may be included in the final parameters. In this example, the lockout period is set to 0.5 hours and the frequency is set to about, e.g., 5 kHz, if testing was done at 5 kHz.

When two dose variations are given, as shown, the subject may be instructed to use both dose 1 and dose 2 initially for several days and then pick the one they feel is more effective in pain reduction.

Figure 6A:
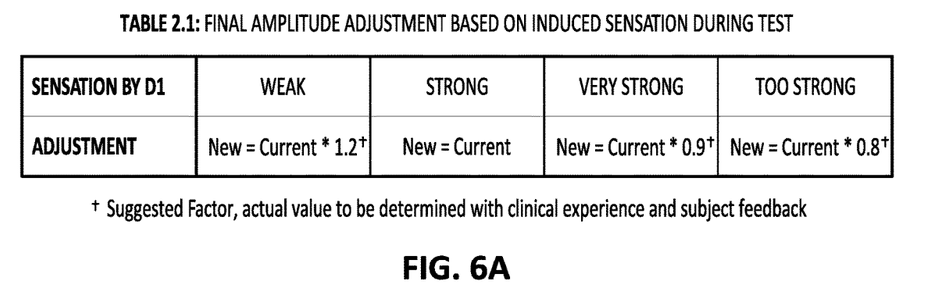
FIGS. 6A-6C are tables that may be used in one method for adjusting therapeutic dose.
Figure 6B:
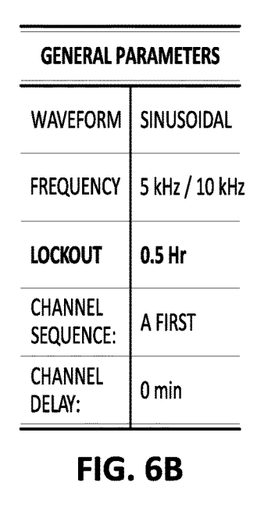
Figure 6C:
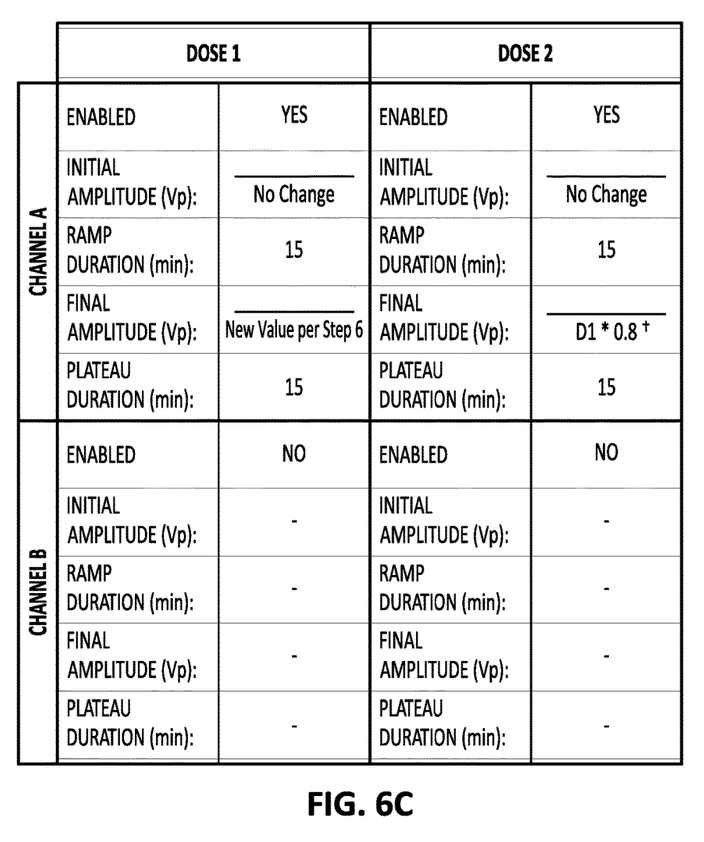

In some variations, the programming (the dose information) may be set, for example every week for 3-4 weeks following the initial setting and periodically thereafter. This may allow the method and/or apparatus to adjust the final amplitude to maximize therapy voltage within tolerable limits of induced sensation. The method described above may be adjusted based on patient-reported sensation. For example, the final voltage may be adjusted as indicated in FIG. 6A (Table 2.1) and the procedure outlined above may be repeated (e.g., to complete the tables shown in FIGS. 6B and 6C).

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of setting therapeutic doses for the treatment of pain using a neuromodulator implanted in a patient, the method comprising:
    applying a test voltage ramp to the patient using the implanted neuromodulator and determining a target sensation intensity modulation voltage that is specific to the patient based on the test voltage ramp applied to the patient, wherein the target sensation intensity modulation voltage corresponds to a maximum patient-tolerable voltage;
    setting a first therapeutic dose for treating the patient based on a first estimated peak modulation voltage, wherein the first estimated peak modulation voltage is estimated as a function of the target sensation intensity modulation voltage and a first therapy ramp-up time to reach the first estimated peak modulation voltage;
    setting a second therapeutic dose for treating the patient based on a second estimated peak modulation voltage, wherein the second estimated peak modulation voltage is estimated as a function of the target sensation intensity modulation voltage and a second therapy ramp-up time to reach the second estimated peak modulation voltage, wherein the second estimated peak modulation voltage is different than the first estimated peak modulation voltage, and wherein the second therapy ramp-up time is different than the first therapy ramp-up time; and
    applying one or both of the first and second therapeutic doses to the patient using the implanted neuromodulator.

2. The method of claim 1, wherein the first estimated peak modulation voltage is estimated as a square root of a product of the target sensation intensity modulation voltage and the first therapy ramp-up time to reach the first estimated peak modulation voltage, and wherein the second estimated peak modulation voltage is estimated as a square root of a product of the target sensation intensity modulation voltage and the second therapy ramp-up time to reach the second estimated peak modulation voltage.

3. The method of claim 2, wherein one of the first and second therapy ramp-up times to the peak modulation voltage is set to be half of a therapeutic dose duration.

4. The method of claim 1, wherein determining the target sensation intensity modulation voltage comprises determining a voltage of the test voltage ramp being applied when a patient-reported feedback indicates a strongest sensation that the patient can tolerate during the application of the test voltage ramp.

5. The method of claim 1, wherein a therapeutic dose duration of the first therapeutic dose is the same as a therapeutic dose duration of the second therapeutic dose.

6. The method of claim 1, wherein a therapeutic dose duration of the first therapeutic dose is different than a therapeutic dose duration of the second therapeutic dose.

7. The method of claim 1, further comprising determining a minimum patient-detectable modulation voltage that is specific to the patient from the test voltage ramp, and further wherein the minimum patient-detectable modulation voltage is used as a starting voltage for one or both of the first and second therapeutic doses.

8. The method of claim 7, wherein determining the minimum patient-detectable modulation voltage comprises receiving patient reported feedback during the application of the test voltage ramp.

9. The method of claim 1, further comprising setting a high-frequency component of the first therapeutic dose to a high-frequency component of the test voltage ramp.

10. The method of claim 9, wherein the high-frequency component of the test voltage ramp applied is between 1 kHz and 100 kHz.

11. The method of claim 1, wherein the target sensation intensity modulation voltage is a product of a ramp-up time used in the test voltage ramp to get to the target sensation intensity modulation voltage and a ramp rate used during the test voltage ramp.

12. A system comprising:
an implantable neuromodulator;
a controller for controlling the application of therapeutic doses for the treatment of pain in a patient by the neuromodulator when implanted in the patient, the controller comprising one or more processors;
memory coupled to the one or more processors, the memory configured to store computer-program instructions, that, when executed by the one or more processors, implement a computer-implemented method, the computer-implemented method comprising:
applying a test voltage ramp to the patient using the implanted neuromodulator and determining a target sensation intensity modulation voltage that is specific to the patient based on the test voltage ramp applied to the patient using a ramp rate over a ramp-up time, wherein the target sensation intensity modulation voltage corresponds to a maximum patient-tolerable voltage;
setting a first therapeutic dose for treating the patient based on a first estimated peak modulation voltage, wherein the first estimated peak modulation voltage is estimated as a function of the target sensation intensity modulation voltage and a first therapy ramp-up time to reach the first estimated peak modulation voltage;
setting a second therapeutic dose for treating the patient based on a second estimated peak modulation voltage, wherein the second estimated peak modulation voltage is estimated as a function of the target sensation intensity modulation voltage and a second therapy ramp-up time to reach the second estimated peak modulation voltage, wherein the second estimated peak modulation voltage is different than the first estimated peak modulation voltage, and wherein the second therapy ramp-up time is different than the first therapy ramp-up time; and
applying one or both of the first and second therapeutic doses to the patient using the implanted neuromodulator.

13. The system of claim 12, wherein the first estimated peak modulation voltage is estimated as a square root of a product of the target sensation intensity modulation voltage and the first therapy ramp-up time to reach the first estimated peak modulation voltage, and wherein the second estimated peak modulation voltage is estimated as a square root of a product of the target sensation intensity modulation voltage and the second therapy ramp-up time to reach the second estimated peak modulation voltage.

14. The system of claim 12, further comprising setting a high-frequency component of one or both of the first and second therapeutic doses to a frequency between 1 kHz and 100 kHz.

15. The system of claim 12, further comprising determining a minimum patient-detectable modulation voltage that is specific to the patient from the test voltage ramp, and further wherein the minimum patient-detectable modulation voltage is used as a starting voltage for one or both of the first and second therapeutic doses.

16. A method of setting one or more therapeutic doses for the treatment of pain using a neuromodulator implanted in a patient, the method comprising:
applying a test voltage ramp to the patient using the implanted neuromodulator and determining a target sensation intensity modulation voltage that is specific to the patient based on the test voltage ramp applied to the patient, wherein the target sensation intensity modulation voltage corresponds to a maximum patient-tolerable voltage;
setting the one or more therapeutic doses for treating the patient based on an estimated peak modulation voltage, wherein the estimated peak modulation voltage is estimated as a function of the target sensation intensity modulation voltage and a therapy ramp-up time to reach the estimated peak modulation voltage; and
applying the one or more therapeutic doses to the patient using the implanted neuromodulator.

17. The method of claim 16, wherein a high-frequency component of the test voltage ramp is between 1 kHz and 100 kHz.

18. The method of claim 16, wherein each of the one or more therapeutic doses comprises a therapeutic dose duration including the therapy ramp-up time to reach the estimated peak modulation voltage and a sustained peak modulation time during which a voltage is sustained at the estimated peak modulation voltage.

* * * * *